United States Patent [19]

Shaw et al.

[11] Patent Number: 4,468,811
[45] Date of Patent: Aug. 28, 1984

[54] TAMPER-EVIDENT CLOSURE FOR BAG

[75] Inventors: Peter M. Shaw, Whitehaven; Friedhelm Dahl, Workington, both of England

[73] Assignee: Smith Brothers (Whitehaven) Limited, England

[21] Appl. No.: 498,215

[22] Filed: May 25, 1983

[30] Foreign Application Priority Data

Mar. 25, 1983 [GB] United Kingdom ............... 8308303

[51] Int. Cl.$^3$ .................. B65D 33/20; B65D 30/08
[52] U.S. Cl. ............................. 383/5; 383/84; 206/632; 206/439
[58] Field of Search ............. 383/84, 5; 206/610, 206/613, 618, 632

[56] References Cited

U.S. PATENT DOCUMENTS 3,754,700  8/1973  Bonk ................................. 206/632
4,276,982  7/1981  Sibrava et al. .................. 383/84 X

FOREIGN PATENT DOCUMENTS 1470786  4/1977  United Kingdom ............... 383/84
2032882  5/1980  United Kingdom ............... 383/5

Primary Examiner—William Price
Assistant Examiner—Sue A. Weaver
Attorney, Agent, or Firm—William A. Drucker

[57] ABSTRACT

A pouch comprises two opposed webs having respective side and bottom portions sealed together thereby leaving an unsealed end whereat one of the opposed webs extends beyond the free edge of the other of the opposed webs to form a flap. The flap is foldable onto over an edge portion of the other web. An area of pressure sensitive adhesive, which is disposed on the flap, extends through a position for normal folding of the flap, so that the flap is foldable within the area covered by the adhesive to bring that latter into direct sealing contact at the flap fold.

The flap is foldable along a rupturable portion which extends across the width of the flap. The relatively readily rupturable portion, which defines a fold line, comprises a perforated line of weakness or a scored line of weakness.

15 Claims, 2 Drawing Figures

TAMPER-EVIDENT CLOSURE FOR BAG

This invention relates to pouches and especially to sterilisable pouches for medical articles, such as surgical instruments.

There has been in recent years a considerable increase in the use of self-seal sterilisable pouches. Various types of pouches are known and have such features as being convenient to use, economical, and needing no special heat sealing equipment or hand tape application. It is of course important in any self-seal sterilisable pouch that an optimum seal integrity in the sealing system is both achieved and maintained over possibly long periods of time, so as to enable the pouch to remain contaminant-proof during such time.

Self-seal sterilisable pouches generally have a flap carrying some form of adhesive which can be folded along a fold line so as to close and seal the pouch. One such type of self-seal sterilisable pouch is disclosed and claimed in U.S. Pat. No. 4,276,982 wherein the flap is folded along a fold line generally defined by the edge of the adhesive nearest the opening or mouth of the pouch.

In such an arrangement there is a risk to the integrity of the seal arising from the incidence of the undesirable unsealable creases in the seal area, which can increase the risk of contamination of an article contained within the pouch.

The present invention therefore sets out to provide a sterilisable pouch with at least a lesser such risk.

According to the present invention, there is provided a pouch which comprises two opposed webs having respective side and bottom portions sealed together thereby leaving an unsealed end whereat one of said opposed webs extends beyond the free edge of the other of said opposed webs to form a flap foldable onto over an edge portion of the other web, the flap having disposed thereon an area of adhesive means extending through a position for normal folding of the flap, so that the flap is foldable within the area covered by said adhesive means to bring that latter into direct sealing contact at the flap fold.

In a preferred embodiment, the flap is foldable along a rupturable portion which extends across the width of the flap. The relatively readily rupturable portion, which defines a fold line, may comprise a perforated line of weakness or a scored line of weakness.

The adhesive means is preferably pressure sensitive. In a preferred embodiment, the adhesive means comprises a pressure sensitive adhesive tape having a release liner or liners, the tape normally being either a single or double coated transfer tape.

The adhesive tape is preferably spaced from the edge of the other of said opposed webs by a distance varying between 4 mm and 6 mm. The spacing may permit a portion of the adhesive tape to contact a portion of the one of said opposed webs, as well as the other of said opposed webs, on folding of the flap along the fold line to close and seal the pouch. Such a contact may serve as a telltale if the pouch has been opened and the seal broken, as the holding or contacting strength of the adhesive will tear the one of said opposed webs if the pouch is opened at the seal area.

The relatively readily rupturable portion is preferably spaced from the edge of the adhesive tape adjacent to the edge of the other of said opposed webs by a distance varying between 2 mm and 4 mm. The spacing may permit a portion of the adhesive tape on one side of rupturable portion to contact a portion of the adhesive tape on the other side of rupturable portion, on folding of the flap along the fold line to close and seal the pouch, so as to provide a secure seal.

The invention will now be described by way of example with reference to the accompanying drawings, in which.

Figure 1:
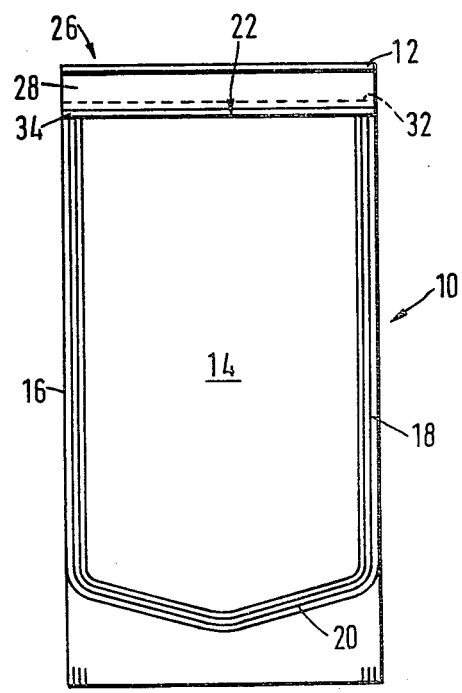
FIG. 1 is a plan view of a pouch according to the invention.

Referring to the drawings, a pouch 10 comprises two opposed webs 12, 14 which are heat-sealed together along their side edges as at 16, 18 and across their width at a bottom portion of the webs as at 20. One end 22 of the pouch is unsealed, thereby forming a mouth so as to permit an article to be placed within the pouch. Web 14 is preferably a laminate of two substantially transparent films, such as polypropylene and polyester bonded together by a tinted adhesive. Web 12 is preferably made of paper, such as machine-glazed bleached kraft paper. We have already proposed such a pouch and it is described and claimed in our co-pending U.K. Patent Application No. 2070514A.

Figure 2:
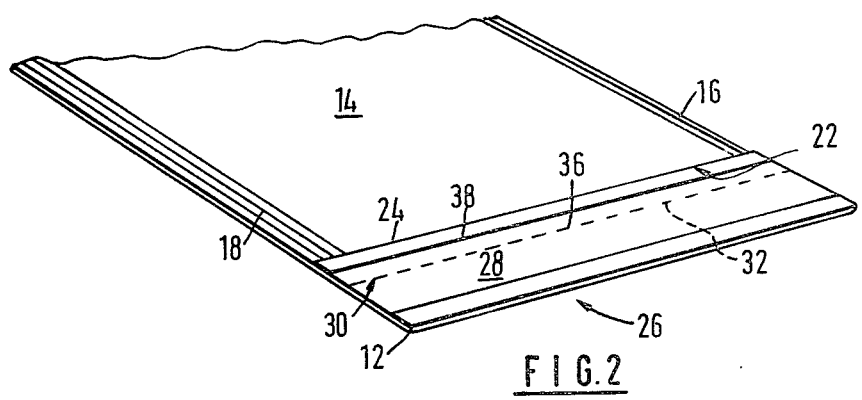
FIG. 2 is an enlarged perspective view of one end of the pouch shown in FIG. 1.

FIGS. 1 and 2 show that the unsealed edge of the web 12 is extended beyond the opposed edge 24 of the web 14 to form a flap 26. The flap 26 has disposed thereon pressure sensitive adhesive means 28 adjacent to and spaced from the edge 24 of the web 14.

The pressure sensitive adhesive means permits the pouch to self seal upon folding the flap and application of pressure along the adhesive area. The adhesive means can be a single or double coated transfer tape having a suitable release liner or liners (not shown).

The adhesive tape or strip 28 is spaced from the edge 24 of the web 14 by a distance varying between 4 mm and 6 mm. In this way, a portion of the adhesive tape 28 can contact a portion 34 of the web 12, as well as the web 14, on folding of the flap 26 to close and seal the pouch. This arrangement can serve as a telltale if the pouch has been opened and the seal broken. The adhesive tape is chosen to maintain seal integrity, and may show evidence of tampering, though it need not be chosen specifically to tear the web. The overall width of the tape can vary between 23 mm and 30 mm, but we prefer the width to be about 25 mm.

The flap 26 is foldable within the area of the flap covered by the adhesive tape 28. As shown in FIGS. 1 and 2, the flap 26 is foldable along a rupturable portion 30 which extends across the width of the flap. The relatively readily rupturable portion, which defines a fold line 32, comprises a perforated line of weakness. The perforations 36 extend through the flap 26 and the adhesive tape 28.

The perforations 36 are spaced from the edge 38 of the adhesive tape adjacent to the edge 24 of the web 14 by a distance varying between 2 mm and 4 mm, preferably by about 3 mm. In this way, a portion of the adhesive tape on one side of the perforations can contact a portion of the adhesive tape on the other side of the perforations, on folding of the flap 26 to close and seal the pouch. A firm contaminant-proof seal is provided, since adhesive contacts adhesive in the seal area.

The extent of the spacing of the perforations 36 from the edge 38 of the adhesive tape also determines the extent to which the flap, on folding along the fold lines, overlies the web 14.

It will be appreciated that other forms of relatively readily rupturable portions may be incorporated into the flap of the pouch of the present invention. For example, such a fold line may comprise a scored line of weakness, or a combination of a perforated/scored line of weakness, through the flap and adhesive tape.

The rupturable fold line 32 of the present invention, and in particular the perforated paper flap 12 and adhesive tape 28, has a more dramatic weakening effect than a pouch flap having a fold line consisting of a crease.

Furthermore, the combined fold line/perforated line of weakness serves to diminish the incidence of undesirable creases in the seal area. Too many creases in the seal area can lead to a deterioration in the integrity of a contaminant-proof seal of a pouch.

We claim:

1. A pouch comprising two opposed webs having respective side and bottom portions sealed together thereby leaving an unsealed end whereat one of said opposed webs extends beyond the free edge of the other of said opposed webs to form a flap foldable onto over an edge portion of the other web, the flap having disposed thereon an area of adhesive means extending through a position for normal folding of the flap, so that the flap is foldable within the area covered by said adhesive means to bring that latter into direct sealing contact at the flap fold.

2. A pouch as claimed in claim 1, wherein the flap is foldable along a rupturable portion which extends across the width of the flap.

3. A pouch as claimed in claim 2, wherein the relatively readily rupturable portion, which defines a fold line, comprises a perforated line of weakness or a scored line of weakness.

4. A pouch as claimed in claim 1, wherein the adhesive means is pressure sensitive.

5. A pouch as claimed in claim 4, wherein the adhesive means comprises a pressure sensitive adhesive tape having at least one release liner, the tape being at least a single coated transfer tape.

6. A pouch as claimed in claim 5, wherein the tape is a double coated transfer tape.

7. A pouch as claimed in claim 5, wherein the adhesive tape is spaced from the edge of the other of said opposed webs by a distance varying between 4 mm and 6 mm.

8. A pouch as claimed in claim 7, wherein the spacing permits a portion of the adhesive tape to contact a portion of the one of said opposed webs, as well as the other of said opposed webs, on folding of the flap along the fold line to close and seal the pouch, said contact serving as a telltale if the pouch has been opened and the seal broken, as the holding or contacting strength of the adhesive will tear the one of said opposed webs if the pouch is opened at the seal area.

9. A pouch as claimed in claim 3, wherein the relatively readily rupturable portion is spaced from the edge of the adhesive tape adjacent to the edge of the other of said opposed webs by a distance varying between 2 mm and 4 mm.

10. A pouch as claimed in claim 9, wherein the spacing permits a portion of the adhesive tape on one side of the rupturable portion to contact a portion of the adhesive tape on the other side of the rupturable portion, on folding of the flap along the fold line to close and seal the pouch, so as to provide a secure seal.

11. A pouch as claimed in claim 6 wherein the adhesive tape is spaced from the edge of the other of said opposed webs by a distance varying between 4 mm and 6 mm.

12. A pouch as claimed in claim 5 wherein the relatively readily rupturable portion is spaced from the edge of the adhesive tape adjacent to the edge of the other of said opposed webs by a distance varying between 2 mm and 4 mm.

13. A pouch as claimed in claim 6 wherein the relatively readily rupturable portion is spaced from the edge of the adhesive tape adjacent to the edge of the other of said opposed webs by a distance varying between 2 mm and 4 mm.

14. A pouch as claimed in claim 12 wherein the spacing permits a portion of the adhesive tape on one side of the rupturable portion to contact a portion of the adhesive tape on the other side of the rupturable portion, on folding of the flap along the fold line to close and seal the pouch, so as to provide a secure seal.

15. A pouch as claimed in claim 13 wherein the spacing permits a portion of the adhesive tape on one side of the rupturable portion to contact a portion of the adhesive tape on the other side of the rupturable portion, on folding of the flap along the fold line to close and seal the pouch, so as to provide a secure seal.

* * * * *